United States Patent [19]
Bolich, Jr. et al.

[11] Patent Number: 6,074,628
[45] Date of Patent: *Jun. 13, 2000

[54] HAIRSPRAY COMPOSITIONS CONTAINING SILICON BLOCK COPOLYMERS

[75] Inventors: Raymond Edward Bolich, Jr., Maineville; Kathleen Bridget Jividen, Lebanon; Sanjeev Midha, Blue Ash; Christopher Todd Morrissey, Mason; Peter Marte Torgerson, Washington Court House, all of Ohio; Jian Zhong Yang, Kobe, Japan

[73] Assignee: Procter & Gamble, Cincinnati, Ohio

[*] Notice: This patent is subject to a terminal disclaimer.

[21] Appl. No.: 08/940,101

[22] Filed: Sep. 29, 1997

Related U.S. Application Data

[63] Continuation-in-part of application No. 08/864,255, May 28, 1997, abandoned, which is a continuation-in-part of application No. 08/842,938, Apr. 25, 1997, abandoned.

[51] Int. Cl.$^7$ .................... A61K 7/06; A61K 7/11
[52] U.S. Cl. .............. 424/47; 424/70.02; 424/70.11; 424/70.12; 424/78.03; 514/63
[58] Field of Search ............... 424/70.02, 70.11, 424/70.12, 78.03, 47; 514/63

[56] References Cited

U.S. PATENT DOCUMENTS

| | | | |
|---|---|---|---|
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,749,565 | 6/1988 | Grollier | 424/70 |
| 4,788,006 | 11/1988 | Bolich et al. | 252/550 |
| 4,814,402 | 3/1989 | Nakashima et al. | 526/245 |
| 4,874,868 | 10/1989 | Bolich et al. | 424/70.11 |
| 4,902,499 | 2/1990 | Bolich, Jr. et al. | 424/70 |
| 4,933,176 | 6/1990 | van Reeth | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,983,377 | 1/1991 | Murphy et al. | 424/47 |
| 4,988,506 | 1/1991 | Mitra et al. | 424/81 |
| 5,002,762 | 3/1991 | Bolich et al. | 424/70.11 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,115,049 | 5/1992 | Imperante et al. | 525/479 |
| 5,120,812 | 6/1992 | O'Lenick, Jr. et al. | 528/28 |
| 5,166,276 | 11/1992 | Hayama et al. | 525/329.7 |
| 5,209,924 | 5/1993 | Garbe et al. | 424/71 |
| 5,219,560 | 6/1993 | Suzuki et al. | 424/63 |
| 5,229,435 | 7/1993 | Sakai et al. | 523/105 |
| 5,258,490 | 11/1993 | Chang | 528/488 |
| 5,294,437 | 3/1994 | Shah et al. | 424/71 |
| 5,523,365 | 6/1996 | Geck et al. | 526/194 |
| 5,565,193 | 10/1996 | Midha et al. | 424/70.12 |
| 5,618,524 | 4/1997 | Bolich, Jr. et al. | 424/70.12 |
| 5,620,684 | 4/1997 | Dupuis | 424/70.12 |
| 5,622,694 | 4/1997 | Torgerson et al. | 424/70.122 |
| 5,632,998 | 5/1997 | Midha et al. | 424/401 |
| 5,653,968 | 8/1997 | Carballada et al. | 424/70.11 |
| 5,653,969 | 8/1997 | Carballada et al. | 424/70.16 |
| 5,658,552 | 8/1997 | Bunning et al. | 424/45 |
| 5,658,557 | 8/1997 | Bolich et al. | 424/70.12 |
| 5,662,892 | 9/1997 | Bolich, Jr. et al. | 424/70.1 |
| 5,665,337 | 9/1997 | Carballada et al. | 424/70.12 |
| 5,667,771 | 9/1997 | Carballada et al. | 424/70.12 |
| 5,730,966 | 3/1998 | Torgerson et al. | 424/70.11 |
| 5,753,216 | 5/1998 | Leitch et al. | 424/70.12 |
| 5,763,548 | 6/1998 | Matyjaszewski et al. | 526/135 |
| 5,807,937 | 9/1998 | Matyjaszewski et al. | 526/135 |

FOREIGN PATENT DOCUMENTS

| | | | |
|---|---|---|---|
| 18835/92 | 6/1996 | Australia | A61K 7/032 |
| 117 360 A1 | 9/1984 | European Pat. Off. | C08L 83/08 |
| 408 311 A2 | 1/1991 | European Pat. Off. | C08F 230/08 |
| 766 957 A1 | 4/1997 | European Pat. Off. | A61K 7/06 |
| 4-359912 | 12/1992 | Japan | C08F 299/08 |
| 4-359913 | 12/1992 | Japan | C08F 299/08 |
| 4-360812 | 12/1992 | Japan | A61K 7/00 |
| 88/05060 | 7/1988 | WIPO | C08F 30/08 |
| 93/23009 | 11/1993 | WIPO | A61K 7/48 |
| 95/03776 | 2/1995 | WIPO | A61K 7/06 |
| 95/04518 | 2/1995 | WIPO | A61K 7/06 |
| 95/06079 | 3/1995 | WIPO | C08G 77/42 |
| 96/32918 | 10/1996 | WIPO | A61K 7/06 |

*Primary Examiner*—Raj Bawa
*Attorney, Agent, or Firm*—William J. Winter; Andrew A Paul

[57] ABSTRACT

The present invention relates to hairspray compositions comprising from about 50% to about 99.9% by weight of an alcohol solvent, and from about 0.1% to about 30% by weight of a silicone-containing adhesive block copolymer having a weight average molecular weight from about 10,000 grams/mole to about 10,000,000 grams/mole and which is formed from the free radical polymerization of an ethylenically unsaturated monomer with select silicone macroinitiators, preferably silicone macroazoinitiators. The hairspray compositions, when dried, preferably have a cohesive strength of greater than about 0.5 kgf/mm$^2$, a total energy absorption per unit volume of greater than about 0.55 kgfmm/mm$^3$, an impact strength of greater than about 7000 ergs, and an improved removeability from hair as defined by a hair stiffness value of from 0 to about 3.5 (0 to 4 scale) and a hair flaking value of from 0 to about 3.5 (0 to 4 scale). These hairspray compositions provide improved hair styling performance, and in particular provide improved maintenance or hold when applied to dry hair and causes minimal or no drooping of the hair during or immediately after application.

33 Claims, 1 Drawing Sheet

HAIRSPRAY COMPOSITIONS CONTAINING SILICON BLOCK COPOLYMERS

This application is a continuation-in-part of Ser. No. 08/864,255, filed on May 28, 1997, now abandoned, which is a continuation-in-part of Ser. No. 08/842,938, filed on Apr. 25, 1997, now abandoned.

TECHNICAL FIELD

The present invention relates to hairspray compositions which provide improved hair style retention characteristics and hair feel. These compositions comprise a silicone-containing adhesive block polymer and at least about 50% by weight of an alcohol solvent.

BACKGROUND OF THE INVENTION

Hair styling compositions are well known and include compositions formulated for and intended for application as shampoos, hairsprays, aerosol mousses, and other formulations known for use in delivering hair styling polymers to the hair. These compositions are typically applied to wet or dry hair, depending on the formulation, and allowed to form thin hair styling films or welds to the applied surface.

Hair styling compositions are commonly formulated as hairsprays intended for application to dry, positioned or styled hair to maintain or hold the position of such dry, styled hair. These hairsprays are typically applied to the hair as pump sprays or from pressurized aerosol canisters.

Such compositions provide temporary setting benefits to dry, styled hair and can usually be removed by water or by the next shampooing. The hair styling materials used in hairspray compositions are generally in the form of resins, gums, and adhesive polymers.

Many hairsprays, however, tend to deposit hair styling material on the hair that leaves the hair either excessively stiff or excessively sticky after the material has been applied to the hair and allowed to dry. Excessively stiff hairsprays are brittle and break down under common stresses such as wind, brushing, combing, and often feel or look unnatural. On the other extreme, excessively sticky hairsprays are more flexible under stress and are not excessively brittle, but leave the hair with a heavy, coated feel and a limp appearance as the hair droops and does not readily maintain or hold the intended style of the hair. These excessively sticky hairsprays also cause the hair to quickly become soiled from dust, dirt, lint, sebum, and other common contaminants that more readily adhere to the sticky hairsprays.

Some hairsprays have been formulated which can be applied to clean, dry hair to maintain or hold the desired hair style, and which are neither excessively stiff or sticky after application. However, many of these hairsprays still cause the hair to droop excessively immediately after application to the dry, styled or positioned hair. The applied hairspray then solidifies on the hair, and then retains the drooped or otherwise limper position of the hair caused by the initial application of the hairspray.

It has now been found that the hairspray compositions of the present invention are especially effective in providing hair styling performance when applied to dry, styled or positioned hair, without causing the hair to be excessively stiff or sticky and without causing the hair to excessively droop immediately after application. These hairspray compositions comprise select silicone-containing adhesive copolymers in combination with an alcohol solvent, wherein the composition contains at least about 50% by weight of the alcohol solvent. The hairspray compositions when dried preferably have a cohesive strength of greater than about 0.5 $kgf/mm^2$, a total energy absorption per unit volume of greater than about 0.55 $kgfmm/mm^3$, and an impact strength of greater than about 7000 ergs.

It has also been found that the preferred hair spray compositions of the present invention have an improved removeability from hair during shampooing, wherein the removeability is defined in terms of hair stiffness and hair flaking values ranging from 0 to about 3.5 (0 to 4 scale) These hair stiffness and flaking values are indirect measures of hair spray removeability. Each of these values are determined in accordance with the methodology defined herein.

It is therefore an object of the present invention to provide hairspray compositions that are neither excessively sticky nor excessively stiff after application, and further to provide such a composition that causes minimal or no drooping of dry, styled or positioned hair after application, and further to provide a hairspray composition having an improved removeability as defined herein.

It is yet another object of the present invention to provide such a composition which comprises select silicone-containing block polymers in combination with high concentrations of an alcohol solvent, and further to provide a method of styling dry, styled or positioned hair without causing excessive drooping of the dry hair immediately after application and without causing the hair to feel excessively stiff or sticky.

SUMMARY OF THE INVENTION

The present invention relates to hairspray compositions comprising from about 50% to about 99.9% by weight of an alcohol solvent, from about 0.1% to about 30% by weight of a silicone-containing adhesive block polymer having a weight average molecular weight of from about 10,000 grams/mole to about 10,000,000 grams/mole and which is formed from the free radical polymerization of an ethylenically unsaturated monomer with a silicone macroinitiator, wherein the silicone macroinitiator contains a chemical group selected from the group consisting of

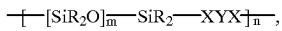

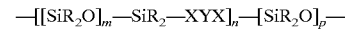

and combinations thereof, wherein each R is independently selected from the group consisting of C1–C10 alkyl, phenyl, C1–C10 alkyl-substituted phenyl, and mixtures thereof; X is a divalent radical; Y is selected from the group consisting of

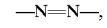

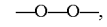

and combinations thereof; m, n, and p are positive integers each independently having a value of 1 or greater; and wherein the silicone macroinitiator has a number average molecular weight from about 500 grams/mole to about 500,000 grams/mole, and wherein the hairspray composition, when dried, preferably has a cohesive strength of greater than about 0.5 $kgf/mm^2$, a total energy absorption per unit volume of greater than about 0.55 $kgfmm/mm^3$, and an impact strength of greater than about 7000 ergs. The hair spray compositions preferably have improved removeability, wherein improved removeability is defined by a hair stiffness value of from 0 to about 3.5 and a hair flaking value of from 0 to 3.5 (0 to 4 scale)

It has been found that these hairspray compositions are especially effective in providing hair styling performance when applied to dry, styled or positioned hair. In particular, these hairspray compositions can be applied to dry, styled or positioned hair without causing the hair to be excessively stiff or sticky after the hairspray has dried onto the hair, and without causing the dry, styled or positioned hair to excessively droop immediately after application of the hairspray composition and before the applied composition solidifies and sets onto the hair.

DETAILED DESCRIPTION OF THE INVENTION

Figure 1:
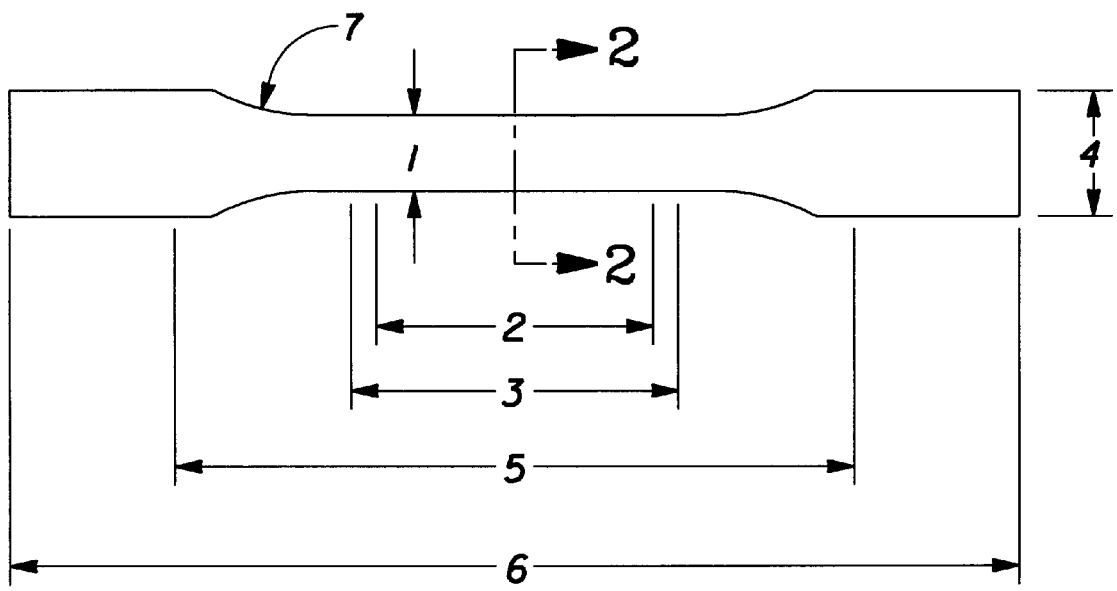
FIG. 1 illustrates an overhead view of a dumbbell-shaped planar dried hairspray film sample useful for measuring the physical properties such as the cohesive strength and total energy absorption per unit volume as described herein.

The hairspray compositions of the present invention comprise select silicone-containing adhesive block polymers in combination with an alcohol solvent. Each of these essential components, as well as preferred or optional components, are described in detail hereinafter.

All percentages, parts and ratios are by weight of the total referenced composition, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "suitable for application to human hair" as used herein, means that the compositions or components thereof so described are suitable for use in contact with human hair and the scalp and skin without undue toxicity, incompatibility, instability, allergic response, and the like.

The term "adhesive" as used herein refers to the silicone-containing block copolymers in the hairspray composition of the present invention that when applied as a solution or dispersion to a surface and dried, e.g., the hair fibers, the block copolymer forms films or welds onto the applied surface. Such a film or weld will have adhesive and cohesive strength, as is understood by those skilled in the art.

The term "kgf" as used herein is a unit of measure characterized as kilogram of force subjected to gravitational acceleration, i.e. 9.82 m/s$^2$.

The hairspray compositions of the present invention can comprise, consist of, or consist essentially of the essential elements of the invention described herein, as well as any of the additional or optional ingredients, components, or other limitations described herein.

Alcohol Solvent

The hairspray compositions of the present invention comprise an alcohol solvent that dissolves or disperses the silicone-containing block copolymer described in detail hereinafter. Concentrations of the alcohol solvent ranges from about 50% to about 99.9%, preferably from about 50% to about 90%, more preferably from about 55% to about 80%, by weight of the hairspray compositions.

Alcohol solvents suitable for use in the hairspray compositions of the present invention are preferably ethanol, n-propanol, isopropanol, and combinations, wherein the selected silicone-containing adhesive block polymer is soluble in the selected alcohol solvent at a concentration of at least about 0.1 mg/mL, preferably at least about 0.5 mg/mL, and more preferably at least about 1 mg/mL, at about 22.7° C.

The hairspray composition may further comprise other additional solvents, including water, provided that the silicone-containing block copolymer remains dissolved or otherwise dispersed in the hairspray composition, and provided that such additional solvents are chemically and physically compatible with the ingredients of the composition and that it does not substantially and unduly impair product performance. The hairspray compositions may further comprise up to about 45% by weight of water, preferably less than about 40%.

It has been found that the alcohol solvent, at the above-described concentrations, when used in combination with the select silicone-containing adhesive block polymers is especially effective at providing improved hair styling performance to the hairspray composition of the present invention. This combination of select polymers and alcohol solvents is even more effective in minimizing or eliminating the undesirable drooping of dry, styled or positioned hair immediately after application to the hair.

Adhesive Block Copolymer

The hairspray composition of the present invention comprises select silicone-containing adhesive block copolymers as defined herein, which help provide the improved hair styling performance to the composition, and which are soluble or dispersible in the alcohol solvent of the hairspray composition. Concentrations of the block copolymers in the hairspray composition ranges from about 0.1% to about 30%, preferably from about 0.5% to about 20%, and more preferably from about 0.5% to about 10%, by weight of the composition.

The silicone-containing adhesive block copolymers selected for use in the hairspray compositions of the present invention are prepared by the free radical polymerization of select silicone containing macroinitiators (described in detail hereinafter) and ethylenically unsaturated monomers. The resulting block copolymers comprise sequentially arranged moieties or blocks which are further composed of smaller repeating units. The silicone-containing adhesive block copolymers herein comprise silicone-containing blocks derived from silicone-containing macroinitiators (hereinafter Block A) and other blocks derived from ethylenically unsaturated monomers as defined herein (hereinafter Block B). These block copolymers are either A-B block structures containing two block segments; A-B-A block structures containing three block segments, -(A-B)$_n$- block structures containing multiple blocks wherein n is an integer having a value of 2 or more, or combinations thereof.

The hairspray compositions of the present invention comprises any one of the of the block structures described above, including mixtures or combinations thereof, and also including combinations thereof with small amounts of unreacted monomer or small amounts of homopolymers derived from the ethylenically unsaturated monomers described herein or the silicone-containing macroinitiators also described herein.

The silicone-containing adhesive block copolymers herein have a weight average molecular weight of from about 10,000 grams/mole to about 10,000,000 grams/mole, preferably from about 20,000 grams/mole to about 1,000,000 grams/mole, more preferably from about 30,000 grams/mole to about 1,000,000 grams/mole, even more preferably from about 60,000 grams/mole to about 750,000 grams/mole, and most preferably from about 70,000 grams/mole and about 750,000 grams/mole.

The silicone-containing adhesive block copolymers for use in the hairspray compositions herein are prepared by free radical polymerization of ethylenically unsaturated monomers and the silicone-containing macroinitiators described herein. Polymerization reactions of this type are generally well known in the polymer art, some descriptions of which are disclosed by M. Mishra, Macromolecular Design: Concept and Practice, Polymer Frontiers International, Inc., pages 313–358 (1994); European Patent Application 766957A1, published Apr. 9, 1997; and Odian, Principles of Polymerization, 3rd edition, John Wiley & Sons, pages 198–334 (1991), which descriptions are incorporated herein by reference in their entirety.

The free radical polymerization reaction referenced herein can be accomplished, for example, by combining the ethylenically unsaturated monomer and the polysiloxane macroinitiator in a reactor along with a sufficient amount of a mutual solvent so that when the reaction is complete the viscosity of the reaction is reasonable. Undesired terminators, especially oxygen, are removed as needed. This can be done by evacuation or by purging with an inert gas, such as argon or nitrogen. The reaction is brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the copolymer by addition of a nonsolvent. The resulting block copolymer can be further purified, as desired, and used in formulating the hairspray composition of the present invention by formulation techniques well known in the art.

The silicone-containing adhesive block copolymers for use herein can also be made by a semi-continuous or continuous process. In the semi-continuous process, two or more additions of monomers or macromonomers are made during the polymerization reaction. This is advantageous when the copolymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

Other examples of silicone-containing block copolymers and methods of making them are described in U.S. Pat. No. 5,523,365, to Geck et al., issued Jun. 4, 1996; U.S. Pat. No. 4,689,289, to Crivello, issued Aug. 25, 1987; U.S. Pat. No. 4,584,356, to Crivello, issued Apr. 22, 1986; Macromolecular Design, Concept & Practice, Ed: M. K. Mishra, Polymer Frontiers International, Inc., Hopewell Jct., N.Y. (1994); and Block Copolymers, A. Noshay and J. E. McGrath, Academic Press, NY (1977), which descriptions are incorporated herein by reference.

Silicone-Containing Macroinitiator

The silicone-containing adhesive block copolymers of the hairspray composition herein comprise from about 2% to about 50%, preferably from about 5% to about 40%, and more preferably from about 10% to about 30%, by weight of silicone-containing blocks, wherein the silicone-containing blocks are derived from the select silicone-containing macroinitiators described herein.

The silicone-containing macroinitiator for use in the hairspray composition of the present invention is selected from the group consisting of the following formulas:

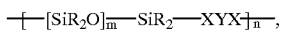

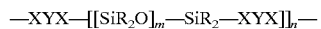

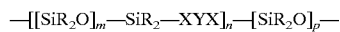

or combinations thereof, wherein each R is independently selected from the group consisting of C1–C10 alkyl, phenyl, C1–C10 alkyl-substituted phenyl, and mixtures thereof, preferably methyl group; each X is a divalent linking group which may be the same or different for any given silicone-containing macroazoinitiator, and which may include the following groups: acyl, alkyl, aryl, amide, alkene, alkyne, ether, ester, sulfone, sulfoxide, thioether, halogen, nitrile and combinations thereof, preferably amide or ester groups for ease of synthesis. Other divalent linking groups can also be used provided that they to not substantially and unduly impair the free radical polymerization reactions described herein.

In the above described macroinitiator formulas, each Y is independently selected from the group consisting of those chemical moieties represented by the following formulas:

or combinations thereof; each of m, n, and p value are positive integers each independently having a value of 1 or greater, preferably m and p have values independently from about 14 to about 700, whereas n has no upper value except that it should not be so large as to limit applicability for practical reasons (viscosity, processing, solvent compatibility, etc.) during the polymerization reaction of the silicone-containing adhesive block copolymers, but is preferably a value of from about 1 to about 10.

The number average molecular weight of silicone-containing macroinitiator is from about 500 grams/mole to about 500,000 grams/mole, preferably from about 2,000 grams/mole to about 250,000 grams/mole, more preferably from about 5,000 grams/mole to about 100,000 grams/mole.

Preferred are the silicone-containing macroinitiators wherein Y is an azo group, even more preferably those silicone-containing macroazoinitiators corresponding to the following formula:

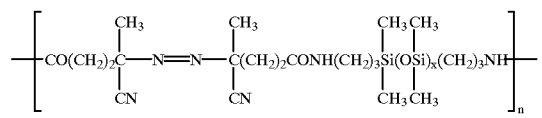

wherein x is an integer having a value of from about 50 to about 150, and n is an integer having a value of from about 4 to about 12, more preferably from about 6 to about 9. Most preferred are those macroazoinitiators represented by the above formula wherein x is an integer having a value of either about 135 or 67, and n is an integer having a value of from about 6 to about 9.

The silicone-containing blocks (Block A) of the block copolymers herein preferably contain at least about 10 repeating monomer units, more preferably at least about 40 monomer units, even more preferably at least about 60 monomer units, wherein each of the repeating monomer units are derived from the select silicone-containing macroinitiators described herein, and the average molecular weight of each silicone-containing block preferably ranges from about 500 grams/mole to about 60,000 grams/mole, more preferably from about 1,000 grams/mole to about 25,000 grams/mole, even more preferably from about 2,000 grams/mole to about 15,000 grams/mole.

Ethylenically Unsaturated Monomer

The silicone-containing adhesive block copolymers of the hairspray composition herein comprise from about 50% to about 98%, preferably from about 60% to about 95%, and more preferably from about 70% to about 90%, by weight of a copolymerizable ethylenically unsaturated monomers.

The blocks (block B) in the silicone-containing adhesive block copolymer are derived from ethylenically unsaturated monomers, wherein block B has a glass transition temperature (Tg value) of more than about −20° C., more preferably more than about −5° C., and also preferably less than about 60° C., more preferably less than about 50° C., and even more preferably less than about 40° C.

The ethylenically unsaturated monomers are copolymerizable with the silicone-containing macroinitiators and contain at least one polymerizable carbon-carbon double bond, which can be mono-, di-, tri- or tetra-substituted. Preferred are vinyl monomers. Either a single type of ethylenically unsaturated monomer or combination of two or more ethylenically unsaturated monomers can be used. The ethylenically unsaturated monomers are selected to meet the requirements of or preferences for the silicone-containing adhesive block copolymers described herein, including solubility in the selected alcohol solvent, glass transition temperatures within the above-described ranges for hair styling or conditioning performance, reactivity with the selected silicone-containing macroinitiator, and so forth.

The ethylenically unsaturated monomers for use in making the silicone-containing adhesive block copolymers may be hydrophilic or hydrophobic, water soluble or water insoluble. These ethylenically unsaturated monomers are preferably hydrophilic monomers, or combinations of hydrophilic and hydrophobic monomers provided that the resulting block copolymer in the hairspray composition has the requisite solubility and other characteristics defined herein. The term "hydrophilic monomers" as used herein refers to monomers which form water soluble homopolymers, whereas the term "hydrophobic monomers" as used herein refers to monomers which form water-insoluble polymers. In this context, the term "water soluble" means that the polymer is soluble in water, ethanol, n-propanol, isopropanol, or combinations thereof, at a concentration of at least about 0.1 mg/ml, preferably at a concentration of at least about 0.5 mg/ml, even more preferably at a concentration of at least about 1 mg/ml, at 22.7° C.

The ethylenically unsaturated monomers when copolymerized into repeating units or blocks (block B) in the silicone-containing adhesive block copolymer herein preferably contains at least about 10 repeating monomers, more preferably at least about 20 repeating monomers, even more preferably at least about 50 repeating monomer units.

Nonlimiting classes of ethylenically unsaturated monomers useful herein include unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and combinations thereof.

Some examples of suitable ethylenically unsaturated monomers include, but are not limited to, acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyidimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, acrylic and methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1hexanol, 1-decanol, 1-dodecanol, 1-hexadecanol, 1-octa decanol, and the like, the alcohols preferably having from about 1 to about 12 carbon atoms; dicyclopentenyl acrylate; 4-biphenyl acrylate; pentachlorophenyl acrylate; 3,5-dimethyladamantyl acrylate; 3,5-dimethyladamentyl methacrylate; 4-methoxycarbonylphenyl methacrylate; trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbornylene; β-pinene; α-pinene; salts of acids and amines listed above, and combinations thereof. The quaternized monomers can be quaternized either before or after the free radical copolymerization reaction with the macroinitiator described hereinafter.

Preferred ethylenically unsaturated monomers include acrylic acid, methacrylic acid, N,N-dimethyl acrylamide, dimethylaminoethyl methacrylate, quaternized dimethylaminoethyl methacrylate, vinyl pyrrolidone, acrylic or methacrylic acid esters of $C_1$—$C_{18}$ alcohols, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, salts of any acids and amines listed above, and combinations thereof.

Neutralized Block Copolymers

The silicone-containing adhesive block copolymers may comprise acidic functionalities, such as carboxyl groups, and are usually used in at least partially neutralized form to promote solubility or dispensability of the block copolymer in the alcohol solvent defined herein. In addition, use of the neutralized form aids in the ability of the hair styling spray compositions to be removed from the hair by shampooing. The extent of such neutralization ranges from about 10% to 100%, more preferably from about 20% to about 90%, even more preferably from about 40% to about 85%, neutralization of the acidic functionalities of the silicone-containing adhesive block copolymer.

Neutralization of the silicone-containing adhesive block copolymer containing acidic functionalities may be accomplished by any conventional or otherwise known technique for affecting such neutralization by using an organic or inorganic base material. Metallic bases are particularly useful for this purpose. Suitable base neutralizers include, but are not limited to, ammonium hydroxides, alkali metal hydroxides, or an alkaline earth metal hydroxides, preferably potassium hydroxide and sodium hydroxide. Examples of other suitable neutralizing agents include, but are not limited to, amines or amino alcohols such as 2-amino-2-methyl-1,3-propanediol (AMPD), 2-amino-2-ethyl- 1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA) and dimethyl stearamine (DMS) and combinations thereof. Preferred are amines and metallic bases.

Neutralization of silicone-containing adhesive block copolymer containing basic functionalities, e.g., amino groups, are likewise preferably at least partially neutralized with an organic or inorganic acid e.g., hydrogen chloride. Neutralization can be accomplished by any conventional or otherwise known technique for accomplishing such neutralization. The preferred extent of neutralization is the same as that described for neutralization of acidic functionalities.

Solubility of the selected silicone-containing adhesive block copolymer, if the selected copolymer contains an acidic or basic functionality, should be determined after the desired acid or base neutralization.

Preferred Silicone-Containing Adhesive Block Copolymers

Nonlimiting examples of preferred silicone-containing adhesive block polymers include, but are not limited to, the following block copolymers derived from the macroazoinitiators which conform to the following formula.

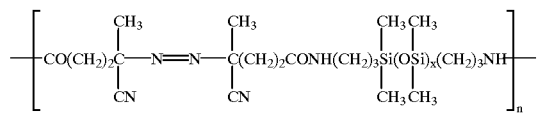

[Poly(dimethyl siloxane)-block-poly(t-butyl acrylate-co-n-butyl acrylate-co-acrylic acid-co-methacrylic acid)]n
  t-butyl acrylate: 40%; n-butyl acrylate: 28%; acrylic acid: 12%; methacrylic acid: 10%; silicone macroazoinitiator (above-described formula, x=135, n is from about 6 to about 9) 10%; Molecular weight of silicone block: 10,000 grams/mole Polymer molecular weight:114,000 grams/mole.

[Poly(dimethyl siloxane)-block-poly(t-butyl acrylate-co-acrylic acid)]n
  t-butyl acrylate: 40%; n-butyl acrylate: 24%; acrylic acid: 21%; silicone macroazoinitiator (above-described formula, x=135, n is from about 6 to about 9)15%; Molecular weight of silicone block: 10,000 grams/mole.
  Polymer molecular weight:86,000 grams/mole.

[Poly(dimethyl siloxane)-block-poly(t-butyl acrylate-co-ethyl acrylate-co-acrylic acid)]n
  t-butyl acrylate: 32%; ethyl acrylate: 33%; acrylic acid: 20%; silicone macroazoinitiator (above-described formula, x=67, n is from about 6–9) 15%. Polymer molecular weight: 110,600 grams/mole. Molecular weight of silicone block: 5000 grams/mole.

The preferred silicone-containing macroazoinitiators described above are available from Wako Chemical U.S.A., Inc., Richmond, Va., U.S.A. as VPS1001 and VPS 0501 (poly(dimethylsiloxane)initiators).

Properties of the Dried Hairspray Compositions

The hairspray compositions of the present invention, when dried, preferably have specific physical properties as defined by cohesive strength, total energy absorption per unit area, impact strength and improved removeability (defined in terms of hair stiffness and flaking values). Each of these preferred physical properties is described in detail hereinafter.

Cohesive Strength (kgf/mm$_2$)

Cohesion is the strength of the bonds formed within a sample, e.g., a dried hairspray composition. The cohesive strength, which is designated as kgf/mm$^2$ (kilograms of force per square millimeter) is the maximum unit stress a material will withstand when being subjected to displacement in tension. Stress is the ratio of measured load (kgxf) to the original cross-sectional area (mm$^2$) of the sample.

The cohesive strength of dried hairspray compositions of the current invention are determined using the following method. This method is based on ASTM Designation: D 638-91, *Standard Test Method for Tensile Properties of Plastics,* Published January 1992, herein incorporated by reference in its entirety. The following test method to measure cohesive strength is similar to the ASTM standard, however, several modifications are made to better represent the tensile properties of the dried hairspray films. The measurements are made at about 22.7° C. and about 50% relative humidity.

The test method, described herein specifically uses a modified dumbbell shape with a thickness equal to about 0.4 mm., and uses an Instron Model Mini-55 (available from Instron Corp., Canton, Mass.) as the testing machine for applying the force to the polymer film samples.

Figure 2:
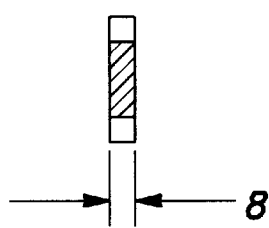
FIG. 2 illustrates a cross-sectional view, showing the thickness of the dumbbell-shaped dried film illustrated in FIG. 1.

A dried film sample is prepared by drying an amount of the hairspray composition (i.e., the silicone-containing adhesive copolymer and solvent selected from the group consisting of water, ethanol, n-propanol, isopropanol, and mixtures thereof, and any additional optional components) in a flat-bottomed aluminum mold coated with PFA (perfluoroalkoxy) Teflon®. The copolymer film is dried at about 22.7° C. and about 50% relative humidity until film has attained a "constant weight". By "constant weight" is meant that there is less than a 1% weight fluctuation in the sample over a period of 24 hours. The drying film should be kept in an area protected from air currents, which could result in non-uniform drying and formation of air bubbles. The copolymer film is cut into a dumbbell shape for testing. The sample should be substantially free of defects, i.e. cracks, chips, tears, etc. FIGS. 1 and 2 illustrate the planar dumbbell shaped film to be used in the tensile testing described herein for the cohesive strength and the total energy absorption per unit volume. FIG. 1 illustrates an overhead view of the dumbbell shaped sample. FIG. 2 illustrates a cross section through the dumbbell shaped sample. The width of the narrow section, 1, of the dumbbell is about 3 mm (1=3 mm). The length of the narrow, 3 mm., section of the dumbbell, 3, is about 13 mm. (3=13 mm.). The gauge length of the narrow section, 2, is the initial film length used in the determination of the strain of the sample. The gauge length is equal to or less than the length of the narrow section, preferably equal to the length of the narrow section (i.e., 2=3). The width of the ends of the dumbbell, 4, are about 10 mm. (4=10 mm.). The distance between end sections of the film, 5, is about 28 mm. (5=28 mm.). The overall length of the film, 6, is about 64 mm. (6=64 mm.). The length of the wide ends of the film is about 18 mm. ((6−5)/2=18 mm.). The transition sections between the wide ends and the narrow section of the film are about 6.5 mm. in length (i.e. (5−3)/2=6.5 mm.). Also the end portions of the narrow, center portion should be smoothly curved to avoid any stress points in the sample. The curve of the transition section, should have a radius, 7, of from about 0.5 in. to about 5 inches, and should join tangentially to the narrow section. The film is formed to a thickness, 8, of 0.4 mm. (8=0.4 mm.). The dumbbell shaped samples are further equilibrated to a "constant weight". By "constant weight" is meant that over a selected 4 day period, there is no more than ±0.2% average weight gain or loss, relative to the dumbbell's measured weight 4 days previous and no more than ±0.2% weight drift should be observed between two consecutive measurements in the four day period of time. The dumbbell should be tested within a 7 day period of reaching this constant weight.

The samples are tested on a calibrated Instron Model Mini-55 tensile tester. Before mounting the sample into the Instron, the length, 3, width, 1, and thickness, 8, of the narrow section of the dumbbell shaped sample are measured to the nearest micron with a calibrated micrometer. The dimensional measurements dimensional measurements are required by ends of the dumbbell samples are clamped into the Instron and pulled at a crosshead rate of 5 mm. per minute. The Instron tester measures the overall forces (e.g., kgf) applied to the film. These forces are spread over the cross sectional area of the narrow section of the film. The cohesive strength of the copolymer is the maximum unit force measured by the Instron divided by the cross sectional area of the narrow portion of the film.

The dried hairspray compositions of the present invention have a cohesive strength of greater than about 0.5 kgf/mm$^2$, preferably greater than about 0.6 kgf/mm$^2$, and more preferably greater than about 0.7 kgf/mm$^2$.

Total Energy Absorption Per Unit Volume (e.g., kgfmm/mm$^{-3}$)

The total energy absorption per unit volume, which is designated as kgfmm/mm$^3$ (kilograms of force millimeters per millimeter cubed), is the ratio of the total energy required to reach the autobreak point (in kgf×mm) to the original volume of the sample (mm$^3$). The total energy required to reach the break point is calculated using standard techniques by determining the area under a load versus displacement curve for the sample. The total energy absorption per unit volume is also known as "toughness" by those skilled in the art of polymer science and materials testing.

The measurements are made at about 22.7° C. and about 50% relative humidity.

The dried hairspray compositions of the present invention preferably have a total energy absorption per unit volume of greater than about 0.55 kgfmm/mm$^3$, more preferably greater than about 0.75 kgfmm/mm$^3$, even more preferably greater than about 1.10 kgfmm/mm$^3$, and most preferably greater than about 2.15 kgfmm/mm$^3$.

Impact Strength

Impact strength is the mean-failure energy (mass X gravity X height) required to produce sample failure, e.g., in a dried hairspray composition. The sample failure is characterized by a crack or split created by the impact of the falling weight that can be seen by the naked eye under normal laboratory lighting conditions.

The impact strength of the dried hairspray compositions of the current invention are determined using the following method. This method is based on ASTM Designation: D 5420-93, *Standard Test Method for Impact Resistance of Flat, Rigid Plastic Specimen by Means of a Striker Impacted by a Falling Weight* (*Gardner Impact*), Published 1995, herein incorporated by reference in its entirety, however, several modifications are made to better represent the impact properties of the dried film. The measurements are made at about 22.7° C. and about 50% relative humidity.

The test method, described herein specifically uses rectangular shaped samples with a thickness equal to about 0.4 mm, and uses a GCA/Precision Scientific Penetrometer modified to drop a blunt faced probe to a distance of 70 mm and equipped with a Precision Scientific solenoid controller for GCA Penetrometer, a blunt faced cylindrical probe with a surface area of 8 mm$^2$ (OK M&T Corp. —part #WSU30), and a ruler which measures in 1 mm increments.

The samples are prepared using the film drying method described above in the cohesive strength measurements. The copolymer film is cut into the rectangular shape, e.g. 10 mm×20 mm.

The thickness of the sample is 0.4 mm. The film thickness of various test samples should be maintained within ±15% of 0.4 mm.

The following measurement process is used. Turn on the solenoid operated probe release controller. The controller should begin to cycle on and off as indicated by a red light. Be sure the probe face is flush with the impact surface so that the sharp edge of the probe does not strike the film. Place a film sample on the Impact Tester over the target area. Direct the metric ruler gently on the film sample. Direct the lightening source across the surface of the sample such that the light source is in the same plane as the surface of the film. Small fractures in the film will reflect light and be easily detected. Move the probe up to desired drop distance. A suggested distance progression is: 1 mm, 3 mm, 5 mm, 10 mm, 15 mm, 20 mm, 25 mm, and further 5 mm increments up to 70 mm. (70 mm is the upper limit of the instrument). Turn on the instrument switch, to drop the probe onto the sample. The first step in the measurement of impact energy is to find the range of probe height necessary to fracture the film. Start at 1 mm for the first step. Continue to move up according to the suggested distance progression until a fracture is observed. When a fracture is observed make a note of it and move to a new sample. The second step in determining impact energy is to set a new sample and start drop at an observed fracture point in the range procedure. Set a new film sample and move the probe to the next lowest setting. If the film fractures, record result and repeat previous step. If the film does not fracture, set a new sample and move to the next distance. Continue to set new samples and increase the drop distance until the film fractures. Continue the procedure until 5 fractures are observed. Calculate the amount of work energy, i.e. the fracture strength using the following formula:

$$W = m \times g \times h,$$

where

W=amount of work energy in ergs, m=mass of probe (59.53 g) (The probe is removable and can be replaced with one of different mass or impact surface area).

g=gravitational constant (980.665 cm/sec$^2$), h=average distance probe travels to impact (cm).

The dried hairspray compositions of the present invention preferably have an impact strength of greater than about 7000 ergs, more preferably greater than about 20,000 ergs, and even more preferably greater than about 50,000 ergs.

Hair Spray Removeability

The adhesive copolymers herein have improved removeability when used in the preferred hairspray embodiments of the present invention. In this context, improved removeability means that the adhesive copolymers are more easily removed from the hair or other applied surface during shampooing.

For purposes of defining the preferred hair spray compositions of the present invention, removeability is determined indirectly by evaluating hair stiffness and the appearance of observable white flakes after treating the hair in accordance with the removeability methodology described hereinafter. It has been found that the removeability of a hair spray formulation after shampooing correlates with the resulting stiffness/softness of the hair and the appearance/nonappearance of white flakes on the hair after a series of shampooing cycles. The hair spray compositions of the present invention have high removeability e.g., reduced stiffness and reduced white flaking. The term "removeability" as used herein therefore refers to hair stiffness values (0–4 scale) and white flaking values (0–4 scale) as measured in accordance with the methodology described hereinafter.

For purposes of the defining the preferred hair spray compositions of the present invention, the removeability of the hair spray compositions is defined as a combination of hair stiffness values and hair flaking values, wherein the hair spray compositions provide hair flaking values ranging from 0 to about 3.5, preferably from 0 to about 2.5, more preferably from 0 to about 2.0, and hair stiffness values ranging from 0 to about 3.5, preferably from 0 to about 2.5, more preferably from 0 to about 2.0.

Methodology: Hairspray Removeability

Removeability of the hairspray composition of the present invention, as indirectly evaluated in terms of hair stiffness and the appearance of white flakes, is determined in accordance with the following methodology. The methodology simulates multiple application and multi-cycle application of hairspray compositions so as to indirectly determine how readily and effectively such hairspray compositions are removed from hair.

The methodology described herein provides a means of evaluating hair switches blindly treated with hairspray embodiments of the present invention. The method by which each hair switch is treated with the hairspray embodiments, and the method by which each treated hair switch is then evaluated for removeability are described in detail below.

Two trained panelists each evaluate identically treated hair switches or sets of hair switches for stiffness and the appearance of white flakes. The panelists then individually assign each of the treated hair switches with a numerical score (0 to 4 scale) for hair stiffness and a numerical score for flaking (0 to 4 scale). The order in which the hair switches are treated with different hair spray embodiments is randomized and conducted round robin. Two identical sets of switches are prepared as described below for each panelist so that each has a fresh set of switches to evaluate. Before evaluating the blindly treated hair switches, each panelist also evaluates (not blinded) an untreated hair switch as a zero reference for hair stiffness and flaking. Each panelist also evaluates a control treated hair switch as a flaking reference (score 4.0) and another control treated hair switch as a hair stiffness reference (score 4.0). The hair stiffness values as defined herein are determined by averaging the hair stiffness scores provided by the two panelist. Likewise, the hair flaking values as defined herein are determined by averaging the hair flaking scores provided by the two panelists.

The hair switches are treated with either an aerosol or non-aerosol hair spray embodiment of the present invention in accordance with the following steps. The hair stiffness reference and the flaking reference are also prepared in accordance with the following steps, except that each is treated with the corresponding hair spray formulations as described hereinafter in Tables 2 and 3.

1) Vertically suspend a clean hair switch (10 inch European virgin brown hair, 20 gram) from its bound end and comb (black rubber comb, 5 inches by 1 inch, ½ fine tooth) through the switch to remove any tangles.

2) If necessary, use a static gun to eliminate any static build-up on the switch.

3) For non-aerosol products, spray the switch from a distance of 4 inches while applying ten pumps of the product to the switch and while moving the atomized spray pattern in a fluid up-and-down motion to cover the entire switch, or for aerosol products, spray each switch from a distance of 6 inches while applying the aerosol stream to the switch for a period of 3 seconds and while moving the aerosol stream in a fluid up-and-down motion to cover the entire switch.

4) Repeat step 3 on the opposite side of the switch.

5) After spraying the opposite side of the switch, hang the treated switch from its bound end to allow it to dry for one hour at ambient temperature, pressure and humidity.

6) Comb the dried switch using a black rubber comb (5 inches ×1 inch, ½ inch fine tooth) by combing away from the bound end of the switch but by initially starting toward the unbound end taking smaller strokes and then gradually taking larger strokes until the comb passes through the entire unbound length of the treated switch.

7) Repeat steps 1 through 6.

8) Wet the treated hair switch with water (+15–20 grain hardness, 38° C., 1 gal/min. water pressure).

9) Apply 1 ml of shampoo ( Table 1: methodology shampoo) along the length of the front of the wet hair switch and apply another 1 ml of the shampoo along the length of the reverse side of the wet hair switch.

10) Gently milk the switch from top to bottom (hand over hand between thumb and fingers) for 15 seconds at 1 stroke per second.

11) Rinse the hair switch with water (38° C., +15–20 grain hardness, 1 gal/min. water pressure) for 15 seconds. Gently squeeze the hair between the first and second fingers, drawing the fingers down the switch after 5 seconds, 10 seconds, and after final rinse.

12) Hang the treated switch and allow it to dry for two hours at 60° C. in a hot box.

13) Remove the dried switches from the hot box.
14) Comb the dried switch using a black rubber comb (5 inches ×1 inch, ½ inch fine tooth) by combing away from the bound end of the switch but by initially starting toward the unbound end taking smaller strokes and then gradually taking larger strokes until the comb passes through the entire unbound length of the treated switch.
15) Repeat steps 1–14.
16) Repeat steps 1–13.
17) A panelist then evaluates the treated switch by feeling it between their first and second fingers of their dominant hand and between their thumb and other fingers for stiffness and resistance to bending, and then assigns to the treated switch a hair stiffness score (0 to 4 scale). The value of the assigned score is relative to the hair stiffness reference score (4) and the untreated reference score (0).
18) The panelist then combs the evaluated switch in accordance with the procedure set forth in Step 14 above, and then visually evaluates the combed switch for white flakes, coating, and white haze and assings it a hair flaking score (0 to 4 scale). The value of the assigned score is relative to the hair flaking reference score (4) and the untreated reference score (0).

TABLE 1

Methodology Shampoo

| Ingredient List | Percent Composition As Added | Percent Composition Chemical Content |
|---|---|---|
| Sodium Laureth Sulfate | 40.0000 | 10.0000 |
| Water - USP Purified | 30.3000 | 30.3000 |
| Sodium Lauryl Sulfate | 29.1000 | 8.0025 |
| Cocamide DEA | .5000 | .4000 |
| Kathon CG | .1000 | .0015 |
| Citric Acid Solution (50% active) | **adj. from 0–1% (note: water level qs. to 100%) | |

TABLE 2

High Flaking Control

| Raw Materials | Percent Composition As Added | Percent Composition Chemical Content |
|---|---|---|
| Octylacrylamide/Acrylates/ Butylaminoethyl Methacrylate Copolymer (National Starch lot AF-6713) | 4.50 | 4.50 |
| Water - USP Purified | 15.50 | 15.50 |
| Ethanol (SDA 40) | 80.00 | 80.00 |

TABLE 3

High Stiffness Control

| Raw Materials | Percent Composition As Added | Percent Composition Chemical Content |
|---|---|---|
| Octylacrylamide/Acrylates/ Butylaminoethyl Methacrylate Copolymer (National Starch lot AF-6713) | 6.00 | 6.00 |
| Aminomethylpropanol, 95% | 1.04 | 0.99 |
| Water - USP Purified | 15.50 | 15.50 |
| Diisobutyl Adipate | 0.20 | 0.20 |
| Ethanol (SDA 40) | 80.00 | 80.00 |

Each of the formulations described in Tables 1–3 are prepared by conventional formulation and mixing techniques.

Optional Ingredients

The hairspray compositions of the present invention may further comprise one or more optional ingredients known or otherwise effective for use in hairsprays and other hair styling compositions. These optional ingredients may be used to improve or otherwise modify aesthetics, performance or stability of the hairspray compositions. Concentrations of such optional ingredients will vary with the type of material added and its intended performance, but will typically and collectively range from about 0.005% to about 50%, more typically from about 0.05% to about 30% by weight of the composition.

Plasticizers for the silicone-containing adhesive block copolymer are especially useful in the hairspray herein. Suitable plasticizers include any known or otherwise effective plasticizer suitable for use in hair care or other personal care compositions, nonlimiting examples of which include glycerin, diisobutyl adipate, butyl stearate, propylene glycol, tri-$C_2$–$C_8$ alkyl citrates, including triethyl citrate and tripropyl, -butyl, -pentyl, etc., analogs of triethyl citrate, and combinations thereof. Preferred is triethyl citrate.

Plasticizers are typically used at concentrations of from about 0.01% to about 10%, preferably from about 0.05% to about 3%, more preferably from about 0.05% to about 1%, by weight of the hairspray composition. Preferably, the weight ratio of silicone-containing block copolymer to the plasticizer is from about 1:1 to about 40:1, preferably from about 2:1 to about 30:1, more preferably from about 3:1 to about 25:1.

Other optional ingredients include an effective amount of a non-surface active ionic strength modifier system for reducing the viscosity of the hairspray composition. Preferred are minimum concentrations of at least about 0.01% by weight of the hairspray composition, and maximum concentrations sufficiently low for the selected system that the silicone-containing adhesive block copolymer remains solubilized or otherwise dispersed in the hairspray composition. As will be understood by those skilled in the art, as the ionic strength of the composition is increased, the solubility of the silicone-containing adhesive block copolymer in the hairspray composition will decrease until it is no longer soluble or dispersible in the composition and will precipitate out of the composition. The upper limit of the ionic strength modifier system level will vary depending upon the particular ionic strength modifier, alcohol solvent, other liquid vehicles, block copolymer, and other ingredients present in the composition. Concentrations of the optional ionic strength modifier are typically range from about 0.01% to about 4%, preferably from about 0.01% to about 2%, more preferably from about 0.01% to about 0.1%, by weight of the composition The optional ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm$^2$. Generally, the ions of the ionic strength modifier system hereof will be characterized by having, at maximum, four or less carbon atoms per charge, preferably two or less carbon atoms, in any aliphatic chain or straight or branched chain organic heterochain.

The optional ionic strength modifier system comprises monomeric ions of the type which are products of acid-base reactions. Thus, basic and acidic ions OH$^-$ and H$^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the hairspray composition. The ionic strength modifiers can be incorporated into the hairspray compositions, for example, by addition of soluble salts, or by addition of mixtures of acids and bases, or by a combination thereof. When such an optional ionic strength modifier system is used, it is a necessary that both anions and cations of the optional ionic strength modifier system be included in the hairspray composition.

Nonlimiting examples of suitable optional cations for use in the compositions are alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, more preferably sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below. Other nonlimiting examples of suitable cations include organic ions, such as quaternary ammonium ions and cationic amines, such as ammonium mono-, di-, and triethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

Other optional ingredients include surfactants (which may be anionic, cationic, amphoteric, or zwitterionic and which include fluorinated surfactants and silicone copolyols), propellants, hair conditioning agents (e.g., silicone fluids, fatty esters, fatty alcohols, long chain hydrocarbons, cationic surfactants, etc.); emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents; sunscreens; preservatives; thickening agents (e.g. polymeric thickeners, such as xanthan gum); and perfume.

Hairspray Products

The hairspray compositions of the present invention are dispensed as sprayed or atomized liquids from any container or package known or otherwise effective for providing such delivery. Such containers or packages will typically be in the form of pump spray dispensers or aerosol canisters, both of which are well known to those skilled in the art.

The hairspray compositions of the present invention further comprises a propellant when dispensed from a pressurized aerosol container. Any propellant or combination of propellants known or otherwise effective for use in such containers, and which are suitable for application to human skin or hair, can be used herein. Suitable propellants include liquifiable gases conventionally used for aerosol containers, most typically volatile hydrocarbon propellants which can include liquified lower hydrocarbons of 3 to 4 carbon atoms such as propane, butane, isobutane, and combinations thereof.

Other suitable propellants include hydrofluorocarbons such as 1,2-difluoroethane (Hydrofluorocarbon 152A) supplied as Dymel 152A by DuPont. Other suitable propellants include dimethylether, nitrogen, carbon dioxide, nitrous oxide, atmospheric gas, and combinations thereof. Preferred are the hydrocarbon propellants and combinations of hydrocarbon propellants, especially isobutane and combinations containing isobutane.

The aerosol propellant may be mixed with the present hairspray compositions and the amount of propellant to be mixed is governed by normal factors well known in the aerosol art. Generally, for liquifiable propellants, the concentration of propellant is from about 10% to about 60%, preferably from about 15% to about 50% , by weight of the total hairspray composition including the propellant.

Other suitable containers or packages include those pressurized aerosol dispensers where the propellant is separated from contact with the hairspray composition. An example of such a package or container would be a two compartment can of the type sold under the tradename SEPRO from American National Can Corp.

Other suitable aerosol dispensers are those characterized by the propellant being compressed air which can be filled into the dispenser by means of a pump or equivalent device prior to use. Examples of such dispensers are described in U.S. Pat. No. 4,077,441, Mar. 7. 1978, Olofsson; U.S. Pat. No. 4,850,577, Jul. 25, 1989, TerStege; and U.S. Ser. No. 07/839,648, Gosselin et al., filed Feb. 21, 1992, which descriptions are incorporated herein by reference. The hairspray compositions of the present invention may also be dispensed in any known or otherwise effective means for delivery to the hair, including any known or otherwise effective atomizing means such as a nonaerosol pump spray device.

Method of Making

The hairspray compositions of the present invention can be made using conventional formulation and mixing techniques. For example, the silicone-containing adhesive block copolymer and the alcohol solvent are combined and mixed together to form a homogeneous solution or dispersion. Other ingredients are then added to the homogenous solution or dispersion and mixed to yield the hairspray composition of the present invention. If the silicone-containing adhesive block copolymer is neutralized, the neutralizer is preferably added prior to addition of other ingredients. The hairspray composition is then packaged in a conventional or otherwise suitable mechanical pump spray device, or alternatively, in the case of aerosol hairspray compositions, the hairspray composition is packaged in a conventional or otherwise suitable aerosol canisters along with an appropriate propellant system.

Method of Use

The hairspray compositions of the present invention may be used in a conventional manner to provide the desired hair styling benefits. Such methods generally involve application of an effective amount of the composition to dry hair which has been arranged or positioned in the desired style. In this context, the term "effective amount" means an amount sufficient to provide the hair hold and style benefits desired, typically an amount ranging from about 0.5 grams to about 30 grams of the composition, depending upon the selected hairspray composition and formulation, dispenser type, length of hair, type of hair style, and so forth. The composition is applied to the hair by spraying or atomizing the composition using a mechanical pump spray device, a pressurized aerosol container, or other appropriate delivery means. The composition is then dried or allowed to dry on the applied surface.

The following Experiments and Examples further illustrate embodiments within the scope of the present invention. They are given solely for the purposes of illustration and are not to be construed as limitations of the present invention as many variations of the invention are possible without departing from its spirit and scope.

EXAMPLES

The following non-limiting examples illustrate specific embodiments of the hairspray compositions of the present invention, and methods of providing hair styling benefits to dry hair using the compositions. It is understood, however, that various additions or modifications of the specific exemplified embodiments can be made without departing from the spirit and scope of the invention. It is intended to cover, in the appended claims, all such modifications that are within the scope of the subject invention.

The following exemplified polymers 1.1 and 1.2 are specific silicone-containing adhesive block copolymers suitable for use in the hairspray compositions of the present invention. Each of these exemplified block copolymers are then incorporated into specific hairspray embodiments of the present invention as Examples 2.1, 2.1, 2.3.

Polymer 1.1
[Poly(dimethyl siloxane)-block-poly(t-butylacrylate-co-acrylic acid)]$_n$.

Place 62.4 parts of t-butyl acrylate, 20.8 parts acrylic acid, 200 parts acetone (as a solvent), and 15 parts isopropanol (as a chain transfer agent) in a roundbottom flask. Separately, dissolve 16.8 parts VPS-1001(poly(dimethyl siloxane)initiator) macroazoinitiator (commercially available from Wako Chemical U.S.A., INC., Richmond, Va.) into 200 parts ethyl acetate and add the solution to an addition funnel. Purge the reaction vessel with argon for approximately one hour. Following the purge, maintain a constant positive pressure on the closed reaction system with argon. Heat the reaction mixture to 58° C. Add the VPS-1001 solution to the reaction flask in a dropwise fashion over the course of one hour. Maintain heating and stirring for 20 hours. Terminate the reaction by opening the reactor to the atmosphere and cooling to room temperature.

The block copolymer is precipitated from the solution by adding one part of the polymer solution to 15 parts water. The resultant polymer is redissolved in acetone and is precipitated again from 15 parts water. The resultant block copolymer is then placed in a vacuum oven for heated drying. Following the drying, the polymer is ground and extracted for 20 hours with hexane using a soxhlet extractor. The polymer is then vacuum dried with heat in an oven. The glass transition temperature of the block B of the resulting polymer is between about −20° C. and 60° C.

Polymer 1.2
[Poly(dimethyl siloxane)-block-poly(t-butyl acrylate-co-n-butyl acrylate-co-acrylic acid-co-methacrylic acid)]n Place 80 parts of t-butyl acrylate, 56 parts n-butyl acrylate, 12 parts acrylic acid, 10 parts methacrylic acid, 400 parts acetone (as a solvent), and 50 parts isopropanol (as a chain transfer agent) in a roundbottom flask. Separately, dissolve 20 parts VPS-1001 (poly(dimethyl siloxane) initiator) macroazoinitiator (commercially available from Wako Chemical U.S.A., INC., Richmond, Va.) into 400 parts ethyl acetate, add to this solution 12 parts acrylic acid and 10 parts methacrylic acid, and add the solution to an addition funnel. Purge the reaction vessel with argon for approximately one hour. Following the purge, maintain a constant positive pressure on the closed reaction system with argon. Heat the reaction mixture to 58° C. Add the VPS-1001 solution to the reaction flask in a dropwise fashion over the course of one hour. Maintain heating and stirring for 20 hours. Terminate the reaction by opening the reactor to the atmosphere and cooling to room temperature.

The block copolymer is precipitated from the solution by adding one part of the polymer solution to 15 parts water. The resultant polymer is redissolved in acetone and is precipitated again from 15 parts water. The resultant block copolymer is then placed in a vacuum oven for heated drying. Following the drying, the polymer is ground and extracted for 20 hours with hexane using a soxhlet extractor. The polymer is then vacuum dried with heat in an oven. The glass transition temperature of the block B of the resulting polymer is between about −20° C. and 60° C.

Example 2

The following examples represent specific aerosol hairspray embodiments of the present invention.

|  | Example Number | | | | | |
|---|---|---|---|---|---|---|
| Component (wt %) | 2.1 | 2.2 | 2.3 | 2.4 | 2.5 | 2.6 |
| Copolymer 1.1 | 5.00 | 4.00 | 3.50 | — | — | — |
| Copolymer 1.2 | — | — | — | 5.00 | 4.00 | 3.50 |
| Isododecane[1] | 0.50 | — | — | 0.50 | — | — |

-continued

| Component (wt %) | Example Number | | | | | |
|---|---|---|---|---|---|---|
| | 2.1 | 2.2 | 2.3 | 2.4 | 2.5 | 2.6 |
| Triethyl citrate[2] | — | — | 0.21 | — | — | 0.21 |
| Diisobutyl adipate | 0.70 | 0.45 | — | 0.70 | 0.45 | — |
| Propylene glycol | — | — | 0.30 | — | — | 0.30 |
| Sodium hydroxide[3] | 1.00 | — | — | 1.00 | — | — |
| Potassium hydroxide[4] | — | 0.94 | 1.20 | — | 0.94 | 1.20 |
| Perfume | 0.10 | 0.10 | 0.10 | 0.10 | 0.10 | 0.10 |
| Water | QS100 | QS100 | QS100 | QS100 | QS100 | QS100 |
| Sodium Benzoate | 0.10 | 0.10 | — | 0.10 | 0.10 | — |
| Ethanol[5] | 56.69 | 57.42 | 72.0 | 56.69 | 57.42 | 72.0 |
| Propellant - Isobutane | — | — | 7.02 | — | — | 7.02 |
| Propellant - n-butane | 10.00 | — | — | 10.00 | — | — |
| Propellant - Dimethyl ether[6] | 10.00 | — | — | 10.00 | — | — |
| Propellant - Hydrofluorocarbon 152a[7] | — | 25.0 | 15.98 | — | 25.0 | 15.98 |

[1]PERMETHYL 99A, from Presperse, Inc., South Plainfield, NJ, USA.
[2]CITROFLEX-2, from Morflex, Inc., Greensboro, NC, USA.
[3]Sodium hydroxide is 30% active.
[4]Potassium hydroxide is 45% active.
[5]SDA 40 (100% ethanol).
[6]DYMEL - A, from Dupont.
[7]DYMEL - 152a, from Dupont.

The exemplified hairspray compositions 2.1–2.6 are prepared as described above, by first mixing the silicone-containing adhesive block copolymer (polymer 1.1 or 1.2) with ethanol, neutralizing the polymer with sodium or potassium hydroxide, then adding sequentially (as applicable) with mixing, isododecane, plasticizer, perfume, and water. If sodium benzoate is used, it is added after water addition. Most preferably a premix of water and sodium benzoate is made and then added after the main water addition. Propellants for aerosol embodiments are charged to aerosol containers after the remainder of the prepared composition has been added.

Example 3

The following examples represent nonaerosol hair spray compositions of the present invention.

| Component (wt %) | Example Number. | | | | | | | |
|---|---|---|---|---|---|---|---|---|
| | 3.1 | 3.2 | 3.3 | 3.4 | 3.5 | 3.6 | 3.7 | 3.8 |
| Copolymer 1.1 | 4.00 | 5.00 | 6.00 | 4.00 | — | — | — | — |
| Copolymer 1.2 | — | — | — | — | 3.00 | 3.50 | 2.50 | 4.00 |
| Isododecane[1] | 1.00 | — | — | — | — | 1.0 | 2.0 | — |
| Diisobutyl adipate | 0.40 | — | 0.90 | 0.55 | — | — | — | 0.40 |
| Sodium hydroxide[2] | 0.96 | 1.20 | 1.44 | — | — | 1.20 | — | 1.35 |
| Potassium hydroxide[3] | — | — | — | 1.21 | 1.00 | — | 0.70 | — |
| Perfume | 0.10 | 0.10 | 0.10 | 0.10 | 0.10 | 0.15 | 0.10 | 0.15 |
| Water | QS100 | QS100 | QS100 | QS100 | QS100 | QS100 | QS100 | QS100 |
| Sodium Benzoate | — | — | — | — | 0.10 | 0.10 | — | 0.10 |
| Ethanol[4] | 76.54 | 71.95 | 81.56 | 71.25 | 79.40 | 69.26 | 78.00 | 55.00 |

[1]PERMETHYL 99A, ftom Presperse, Inc., South Plainfield, NJ, USA.
[2]Sodium hydroxide is 30% active.
[3]Potassium hydroxide is 45% active.
[4]SDA 40 (100% ethanol).

The exemplified hairspray compositions 3.1–3.8 are prepared as described above, by first mixing the silicone-containing adhesive block copolymer (polymer 1.1 or 1.2) with ethanol, neutralizing the polymer with sodium or potassium hydroxide, then adding sequentially (as applicable) with mixing, isododecane, plasticizer, perfume, and water. If sodium benzoate is used, it is added after water addition. Most preferably a premix of water and sodium benzoate is made and then added after the main water addition.

Each of the exemplified hairspray compositions in Examples 2 and 3 are specific embodiment of the hairspray compositions of the present invention, and provide improved hair styling performance when applied to dry, styled or positioned hair, and in particular provide improved maintenance or hold when applied to dry hair and causes minimal or no drooping of the hair during or immediately after application.

Each of the exemplified hair spray compositions in Examples 2 and 3 also provide improved removeability from hair, and when evaluated by the removeability methodology described herein, provide a hair stiffness value of less than 2.0 and a hair flaking value of less than 2.0.

What is claimed is:

1. A hairspray composition comprising:
   (a) from about 50% to about 99.9% by weight of an alcohol solvent;
   (b) from about 0.1% to about 30% by weight of an adhesive block copolymer having a weight average molecular weight from about 10,000 grams/mole to about 10,000,000 grams/mole and which is formed from the free radical polymerization of an ethylenically unsaturated monomer with a silicone macroinitiator selected from the group consisting of

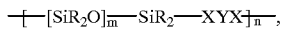

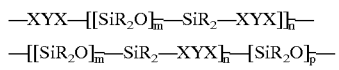

and combinations thereof, wherein each R is independently selected from the group consisting of C1–C10 alkyl, phenyl, C1–C10 alkyl-substituted phenyl, and mixtures thereof, X is a divalent radical, Y is selected from the group consisting of

and combinations thereof; and m, n, and p are positive integers independently having a value of 1 or greater; and wherein the silicone macroinitiator has a number average molecular weight from about 500 grams/mole to about 500,000 grams/mole, and the ethylenically unsaturated monomers are copolymerizable and form one or more polymeric blocks within the adhesive block copolymer having a Tg value of from about −20° C. to about 60° C.

2. The hairspray composition of claim 1 wherein the alcohol solvent is selected from the group consisting of ethanol, n-propanol, isopropanol, and mixtures thereof, and wherein the adhesive block copolymer is solubilized in the hairspray composition.

3. The composition of claim 2 wherein the silicone macroinitiator is a silicone macroazoinitiator where Y is an azo group.

4. The composition of claim 3 wherein the block copolymers comprise from about 60% to about 95% by weight of the copolymerized ethylenically unsaturated monomers, and from about 5% to about 40% by weight of the copolymerized silicone macroinitiators.

5. The composition of claim 3 wherein m has a value of from about 14 to about 700, n has a value of from about 1 to about 10, and silicone macroazoinitiator has a number average molecular weight of from about 5,000 grams/mole to about 100,000 grams/mole.

6. The hairspray composition of claim 3 wherein the weight average molecular weight of the adhesive block copolymer is from about 70,000 grams/mole to about 750,000 grams/mole.

7. The hairspray composition of claim 3 wherein the composition, when dried, has a cohesive strength of greater than about 0.5 kgf/mm², a total energy absorption per unit volume of greater than about 0.55 kgfmm/mm³ and an impact strength of greater than about 7000 ergs.

8. The hairspray composition of claim 7 wherein the composition, when dried has a cohesive strength of greater than about 0.6 kgf/mm², a total energy absorption of greater than about 0.75 kgfmm/mm³, and an impact strength of greater than about 20,000 ergs.

9. The hairspray composition of claim 8 wherein the composition, when dried, has a cohesive strength of greater than about 0.7 kgf/mm², a total energy absorption of greater than about 1.10 kgfmm/mm³, and an impact strength of greater than about 50,000 ergs.

10. The hairspray composition of claim 3 wherein the ethylenically unsaturated monomer is a vinyl monomer selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

11. The hairspray composition of claim 10 wherein the vinyl monomer units are selected from the group consisting of acrylic acid, methacrylic acid, N,N-dimethyl acrylamide, dimethylaminoethyl methacrylate, quaternized dimethylaminoethyl methacrylate, vinyl pyrrolidone, acrylic or methacrylic acid esters of $C_1$–$C_{18}$ alcohols, styrene, alpha-methylstyrene, t-butylstyrene, vinyl acetate, vinyl propionate, vinyl chloride, vinylidene chloride, vinyl toluene, butadiene, cyclohexadiene, ethylene, propylene n-butyl methacrylate, isobutyl methacrylate, t-butyl acrylate, t-butyl methacrylate, 2-ethylhexyl methacrylate, methyl methacrylate, salts of any acids and amines listed above, and combinations thereof.

12. The hairspray composition of claim 3 wherein the composition is dispensed from a mechanical spray pump device.

13. The hairspray composition of claim 3 wherein the composition is dispensed from a pressurized aerosol canister.

14. A method of styling hair comprising the step of applying to the dry, positioned hair an effective amount of the composition of claim 1.

15. A hairspray composition comprising:
   (a) from about 50% to about 99.9% by weight of an alcohol solvent;
   (b) from about 0.1% to about 30% by weight of an adhesive block copolymer having a weight average molecular weight from about 20,000 grams/mole to about 1,000,000 grams/mole and which is formed from the free radical polymerization of an ethylenically unsaturated monomer with a silicone macroazoinitiator which conforms to the formula

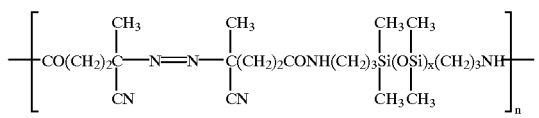

wherein x is an integer having a value of from about 50 to about 150, and n is an integer having a value of from about 4 to about 12, and the ethylenically unsaturated monomers are copolymerizable and form one or more polymeric blocks within the adhesive block copolymer having a Tg value of from about −20° C. to about 60° C.

16. The hairspray composition of claim 15 wherein the alcohol solvent is selected from the group consisting of ethanol, n-propanol, isopropanol, and mixtures thereof, and wherein the adhesive block copolymer is solubilized in the hairspray composition.

17. The composition of claim 16 wherein the block copolymers comprise from about 60% to about 95% by weight of the copolymerized ethylenically unsaturated monomers, and from about 5% to about 40% by weight of the copolymerized silicone macroinitiators.

18. The hairspray composition of claim 16 wherein the weight average molecular weight of the adhesive block copolymer is from about 70,000 grams/mole to about 750,000 grams/mole.

19. The hairspray composition of claim 16 wherein the composition, when dried, has a cohesive strength of greater than about 0.5 kgf/mm$^2$, a total energy absorption per unit volume of greater than about 0.55 kgfmm/mm$^3$ and an impact strength of greater than about 7000 ergs.

20. The hairspray composition of claim 19 wherein the composition, when dried has a cohesive strength of greater than about 0.6 kgf/mm$^2$, a total energy absorption of greater than about 0.75 kgfmm/mm$^3$, and an impact strength of greater than about 20,000 ergs.

21. The hairspray composition of claim 20 wherein the composition, when dried, has a cohesive strength of greater than about 0.7 kgf/mm$^2$, a total energy absorption of greater than about 1.10 kgfmm/mm$^3$, and an impact strength of greater than about 50,000 ergs.

22. The hairspray composition of claim 16 wherein the ethylenically unsaturated monomer is a vinyl monomer selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

23. The hairspray composition of claim 22 wherein the vinyl monomer units are selected from the group consisting of acrylic acid, methacrylic acid, N,N-dimethyl acrylamide, dimethylaminoethyl methacrylate, quaternized dimethylaminoethyl methacrylate, vinyl pyrrolidone, acrylic or methacrylic acid esters of $C_1$–$C_{18}$ alcohols, styrene, alpha-methylstyrene, t-butylstyrene, vinyl acetate, vinyl propionate, vinyl chloride, vinylidene chloride, vinyl toluene, butadiene, cyclohexadiene, ethylene, propylene n-butyl methacrylate, isobutyl methacrylate, t-butyl acrylate, t-butyl methacrylate, 2-ethylhexyl methacrylate, methyl methacrylate, salts of any acids and amines listed above, and combinations thereof.

24. The hairspray composition of claim 16 wherein the composition is dispensed from a mechanical spray pump device.

25. The hairspray composition of claim 16 wherein the composition is dispensed from a pressurized aerosol canister.

26. A method of styling hair comprising the step of applying to dry, positioned hair an effective amount of the composition of claim 15.

27. A method of styling hair comprising the step of applying to dry, positioned hair an effective amount of the composition of claim 1.

28. A composition according to claim 1 wherein the composition is a hairspray composition which provides a hair stiffness value of from 0 to about 3.5 and a hair flaking value of from 0 to 3.5.

29. A composition according to claim 28 wherein the hair spray composition provides a hair stiffness value of from 0 to about 2.5 and a hair flaking value of from 0 to 2.5.

30. A composition according to claim 29 wherein the hair spray composition provides has a hair stiffness value of from 0 to about 2.0 and a hair flaking value of from 0 to about 2.0.

31. A composition according to claim 15 wherein the composition is a hairspray composition which provides a hair stiffness value of from 0 to about 3.5 and a hair flaking value of from 0 to 3.5.

32. A composition according to claim 31 wherein the hair spray composition provides a hair stiffness value of from 0 to about 2.5 and a hair flaking value of from 0 to 2.5.

33. A composition according to claim 32 wherein the hair spray composition provides has a hair stiffness value of from 0 to about 2.0 and a hair flaking value of from 0 to about 2.0.

\* \* \* \* \*